(12) United States Patent
Ataullakhanov et al.

(10) Patent No.: US 9,958,430 B2
(45) Date of Patent: May 1, 2018

(54) DEVICE FOR MONITORING SPATIAL COAGULATION OF BLOOD AND OF COMPONENTS THEREOF

(71) Applicant: OBSCHESTVO S OGRANICHENNOY OTVETSTVENNOSTYU <<GEMATOLOGICHESKAYA KORPORATSIYA>>, Moscow (RU)

(72) Inventors: Fazoil Inoyatovich Ataullakhanov, Moscow (RU); Vasilii Ivanovich Sarbash, Moscow (RU); Mikhail Aleksandrovich Panteleev, Moscow (RU); Sergey Sergeevich Karamzin, Moscow (RU)

(73) Assignee: OBSCHESTVO S OGRANICHENNOY OTVETSTVENNOSTYU <<GEMATOLOGICHESKAYA KORPORATSIYA, Moscow (RU)

( * ) Notice: Subject to any disclaimer, the term of this patent is extended or adjusted under 35 U.S.C. 154(b) by 37 days.

(21) Appl. No.: 14/421,037

(22) PCT Filed: Jul. 9, 2013

(86) PCT No.: PCT/EA2013/000007
§ 371 (c)(1),
(2) Date: Feb. 11, 2015

(87) PCT Pub. No.: WO2014/026697
PCT Pub. Date: Feb. 20, 2014

(65) Prior Publication Data
US 2015/0204841 A1 Jul. 23, 2015

(30) Foreign Application Priority Data

Aug. 15, 2012 (EA) .................................. 201201022

(51) Int. Cl.
*G01N 33/49* (2006.01)
*G01N 21/03* (2006.01)
(Continued)

(52) U.S. Cl.
CPC .............. *G01N 33/49* (2013.01); *B01L 99/00* (2013.01); *G01N 21/0332* (2013.01);
(Continued)

(58) Field of Classification Search
CPC .. C12Q 1/56; G01N 21/6408; G01N 21/6456; G01N 2333/974; G01N 33/49
(Continued)

(56) References Cited

U.S. PATENT DOCUMENTS 3,972,614 A * 8/1976 Johansen ............... G01N 1/286
356/36
4,338,627 A * 7/1982 Stapleton ................. H04N 5/33
250/332
(Continued)

FOREIGN PATENT DOCUMENTS

RU 2149403 C1 5/2000
RU 2343456 C1 1/2009
(Continued)

OTHER PUBLICATIONS

International Search Report with English Translation for International Patent Application No. PCT/EA2013/000007 dated Oct. 11, 2013, 5 pages.

*Primary Examiner* — Dennis White
*Assistant Examiner* — Bryan Kilpatrick
(74) *Attorney, Agent, or Firm* — Volpe and Koenig, P.C.

(57) ABSTRACT

The invention relates to the field of medicine and biology. A device for monitoring of spatial coagulation of blood and its uses for diagnostic and research purposes is described. The device includes a thermostatically controlled chamber, at
(Continued)

least one means of illumination, a means of recording connected to the thermostatically controlled chamber. The thermostatically controlled chamber includes a cuvette to place a sample of a test medium, a light trap, and is filled with a substance suitable for temperature regulation. The light trap is formed by geometry of the inner surfaces of the thermostatically controlled chamber.

8 Claims, 1 Drawing Sheet

(51) Int. Cl.
  *G01N 21/82* (2006.01)
  *B01L 99/00* (2010.01)
  *C12Q 1/56* (2006.01)
(52) U.S. Cl.
  CPC .......... *G01N 21/82* (2013.01); *B01L 2300/14* (2013.01); *B01L 2300/185* (2013.01); *C12Q 1/56* (2013.01); *G01N 2201/0642* (2013.01)

(58) Field of Classification Search
  USPC .................................. 422/73; 435/13, 288.7
  See application file for complete search history.

(56) References Cited

U.S. PATENT DOCUMENTS

2009/0104637 A1    4/2009  Ismagilov et al.
2010/0261211 A1*  10/2010  Ataullakhanov .. G01N 33/4905
                                                      435/13

FOREIGN PATENT DOCUMENTS

| RU | 2391665 C1 | 6/2010 |
| RU | 2395812 C2 | 7/2010 |
| WO | 2009055940 A1 | 5/2009 |

* cited by examiner

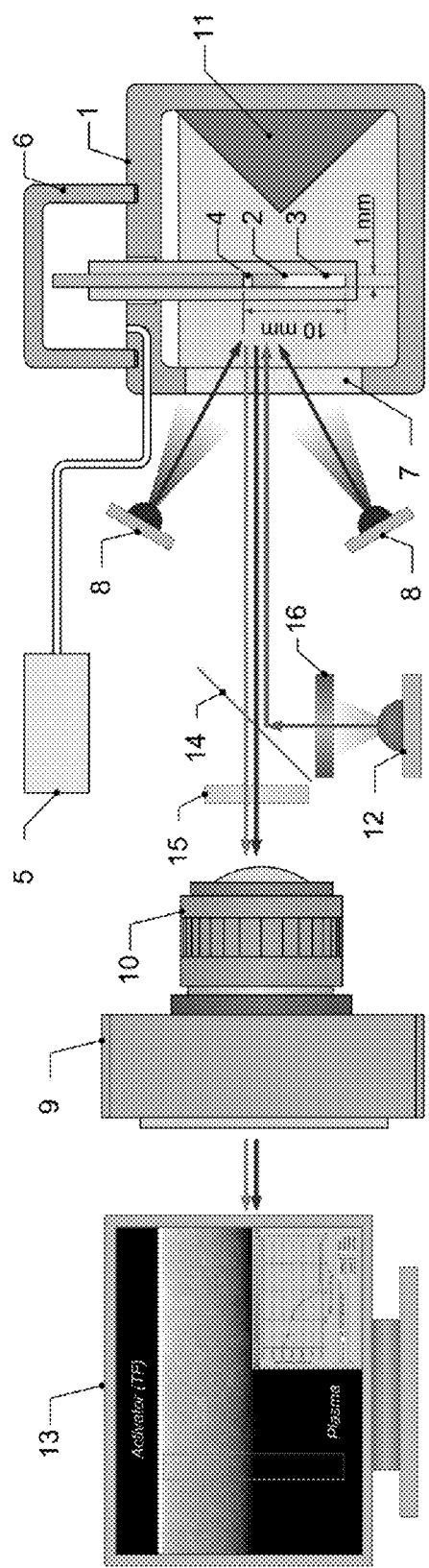

DEVICE FOR MONITORING SPATIAL COAGULATION OF BLOOD AND OF COMPONENTS THEREOF

CROSS REFERENCE TO RELATED APPLICATIONS

This application is a 35 U.S.C. § 371 national phase application of PCT/EA2013/000007, which was filed Jul. 9, 2013, and claims the benefit of Eurasian patent application No. 201201022, which was filed Aug. 15, 2012, both of which are incorporated herein by reference as if fully set forth.

FIELD OF INVENTION

The present technical decision relates to medicine and biology and can be used, in particular, for diagnostic and research purposes to determine coagulation characteristics of blood and its components, as well as in biotechnology and in fundamental biological research.

BACKGROUND

Studies of coagulation of blood and its components are of great practical interest because they do not only allow certain diseases to be diagnosed but also make it possible to assess the activity of preparations affecting blood coagulation parameters. Various devices for determining coagulation rate in whole blood and in plasma are known from the background art. However, up to this day, these studies have been designed in a homogenous system with permanent mixing. As the whole volume of plasma is permanently mixed from the beginning of the test and until the end thereof, all coagulation factors formed during the process of formation of a plasma clot are homogenously distributed in the test medium, and the clot formation is ongoing simultaneously in the whole volume of the test sample. From the physiological point of view, this process is fundamentally different from conditions of clot formation in vivo.

From the background art, we know an apparatus for monitoring the spatial fibrin clot formation disclosed in international application PCT/CH2007/000543 (international publication WO 2009/055940, cl. G01N 33/49, published on May 7, 2009). The apparatus contains a cuvette assembly consisting of a cuvette and an insert with coagulation activator immobilized on the bottom end of the insert. The cuvette assembly is placed in a holder comprising a thermostat for thermal stabilization of the cuvette and devices for fixing the cuvette inside the thermostat. The thermostat is filled with an at least partly transparent fluid. The said apparatus allows registering of the process of formation of a fibrin clot being the final product of work of the coagulation system without providing a possibility to register the process of formation and spatial distribution of other coagulation factors regulating the process of spatial growth of a fibrin clot. The closest analog to the disclosed solution is the device for investigation of coagulation characteristics of blood and its components (patent RU 2395812, cl. G01N33/49, published on Jul. 27, 2010) comprising a thermostatically controlled chamber filled with fluid and accommodating a cuvette with a test sample and an insert with the immobilized coagulation activator, a means of illumination to lighten the contents of the cuvette and the clot formed close to the lower end of the insert, and a digital camera; the device is connected with a computer to process the obtained data.

Disadvantages of the said device include formation of gas bubbles in the test samples and in the fluid, within the registration area, during heating of the test samples in a thermostatically controlled chamber: these bubbles distort the light scattering signal from the fibrin clot. Moreover, the device contains a means of illumination with only one wavelength, for example, red light, which prevents studying spatiotemporal distribution of proteolytic enzymes, for example, with fluorescent methods, simultaneously with the study of fibrin clot formation.

SUMMARY

The technical result which can be obtained through realization of the claimed solution is the enhancement of the method accuracy and reliability as to the definition of parameters of spatial coagulation of blood and its components necessary to diagnose a number of blood disorders, as well as the possibility to determine a number of additional parameters which have not been studied earlier.

The object solved by the disclosed solution is to exclude the influence of gas bubbles within the test sample and the thermostatically controlled fluid on the test process itself (for example, blood coagulation) and on the processing of recorded data while it influences the test integrity and the accuracy of obtained results, as well as to receive new information about the coagulation process and its specific parameters.

The object is resolved by creating a device for monitoring of spatial coagulation of blood and its components including a thermostatically controlled chamber filled with fluid inside of which are installed: a cuvette to place a sample of a test medium, at least one means of illumination and a means of recording equipped with a light trap formed by geometry of the inner surfaces of the thermostatically controlled chamber, and a means of pressure regulation connected with the thermostatically controlled chamber or the cuvette.

As well as by the fact that the device contains at least one further means of illumination.

As well as by the fact that the device contains optical elements which direct, focus and provide spectral correction of the illumination.

As well as by the fact that the device contains an additional control unit of the means of illumination, recording and pressure regulation manufactured to provide a possibility to synchronize the work of the said means.

As well as by the fact that the device contains an additional connection with the means of processing of the test results.

BRIEF DESCRIPTION OF THE DRAWING

FIG. 1 shows schematic representation of the claimed device.

DETAILED DESCRIPTION OF THE PREFERRED EMBODIMENTS

The claimed device contains a thermostatically controlled chamber 1 manufactured with the possibility of temperature regulation and filled with fluid. There is a possibility to provide different types of thermostatic control including water and air thermostatic control as well as thermostatic control involving the use of gel; by the way, it has to be taken into account that the test medium must remain transparent for radiation. Water thermostatic control is preferable. During thermostatic control, permanent temperature is maintained. Cuvette 2 is placed inside of the said chamber 1. Cuvette 2 can be manufactured with at least one channel 3. A test medium sample is placed in the channel 3. A test medium sample can be represented by biological fluid of a mammal (human or animal), such as blood plasma, whole blood, platelet poor plasma or platelet rich plasma. Moreover, the sample can contain mixes of purified natural, synthetic or recombinant proteins and/or other preparations/reagents with hemostatic activity. Insert 4 with an agent applied on its bottom end and facilitating the initiation of the studied process, for example, of coagulation, can be placed in the said cuvette 2. The following agents can be used to facilitate the initiation of the coagulation process: a protein, the so-called tissue factor (thromboplastin) immobilized by different means on the front surface of the insert 4 or directly on the inner surface of the cuvette 2 at a predefined place; as well as other organismic agents such as preparations of cells and tissues. Other thrombogenic agents, such as glass, kaolin, etc., can also be used as an activator.

A major disadvantage of devices known from the background art is distortion of monitoring parameters caused by formation of gas bubbles in the sample as well as in the fluid inside the thermostatically controlled chamber 1 during heating. In order to eliminate the disadvantage, the authors proposed to provide the claimed device with a means 5 of regulation and maintenance of stable pressure during the test. For this purpose, the means 5 of pressure regulation is connected with the thermostatically controlled chamber 1. The means 5 of pressure regulation, in a particular case of manufacturing, can be represented by an air pump connected through a return valve to the inner (pressure-sealed) part of the thermostatically controlled chamber 1 and a pressure sensor measuring pressure in the mentioned chamber 1. Based on the pressure sensor readings, the control unit (not shown in FIG. 1) provides control of the air pump (switches it on/off). The pump is connected to the thermostatically controlled chamber 1 through the pressure line, for example formed by pipes into which is built the return valve preventing eventual pressure release from the thermostatically controlled chamber 1 through the air pump. The valve can be passive mechanic or electromechanical, regulated by the control unit. Upon pressure sealing of the thermostatically controlled chamber 1 and under command of the control unit, the pump switches on to start pressurization in the chamber 1; after reaching the targeted pressure measured by the pressure sensor, the pump switches off. During the test, the targeted pressure is maintained by switching the pump on/off when the pressure falls below the targeted level.

While maintaining the targeted pressure, pressure sealing of the thermostatically controlled chamber 1 is provided. The pressure sealing can be provided, for example, using the means of pressurization 6 of the inner part of the thermostatically controlled chamber 1. The means of pressurization can be represented by a cover, a cup, a shutter, or any other common means. At the same time, the means of pressurization 6 can be mechanic, closed by the operator, or electromechanical, commanded by the control unit.

Moreover, the pressure can be produced directly in the cuvette 2. Then, the means 5 of pressure regulation provides pressure supply into the cuvette 2, and the pressure line (pipes) is connected with the said cuvette.

It was established that the elimination of bubbles is possible when excess pressure as to the atmospheric one, preferably from 0.2 to 0.5 atm, is maintained during the entire test.

The thermostatically controlled chamber 1 is equipped with a transparent window 7 through which at least one means of illumination 8 illuminates the test sample and the clot formed therein. LEDs or any other sources of radiation of the required spectral range (for example, bulbs with optical filters) can be used as the means of illumination. The image of the growing clot (light scattering from the clot) is fixed by the means of registration 9, for example, a digital camera equipped with a lens 10. In order to improve quality of the registered image (correlation signal/background) as well as to monitor additional parameters of coagulation in the thermostatically controlled chamber 1, the light trap 11 is provided. The said light trap 11 is used to reduce background radiation. The background radiation is all radiation except the one scattered in direction of the means of registration by the clot or any other studied structure able to scatter light. The light trap 11 can be manufactured in different ways, amongst others formed by specific geometry of the inner surfaces of the thermostatically controlled chamber, in particular represented by a flattened cone. It can also be formed by conferring light absorbing features to the inner surfaces of the chamber, for example, by darkening them and making them somewhat rough. The geometry and the optical features of the light trap 11 were figured out so as to provide repeated re-reflection and absorption of the background radiation.

In turn, the means of registration 9 is electrically and informatively connected with the means 13 of processing of the test results, for example, a computer. The means of illumination and the means of registration are manufactured with the possibility of regulation by the control unit (not shown in FIG. 1).

The appearance of chromogenic, and later of fluorogenic substrates, allowed obtaining new information about the functioning principles of the coagulation system. When adding the said substrate into the test sample containing a proteolytic enzyme, the latter cleaves a signal mark from the substrate. The mark is able either to change optical density of the test sample (coloring substrate) or to fluoresce when illuminated (fluorogenic substrate). It is possible to figure out the spatial distribution of the corresponding proteolytic enzyme based on the spatial distribution of the signal mark using the equations of the reaction-diffusion-convection type.

When using fluorogenic substrates, the claimed device is provided with at least one additional means of illumination 12 illuminating the sample of the test medium at determined moments of time with the exciting radiation in order to excite fluorescence of the mark. The means of illumination 12 provides supply of radiation, preferably perpendicularly to the cuvette wall 2 through optical elements which direct, focus and provide spectral correction of the illumination, for example, using the mirror 14 as well as the filters of emission 15 and of excitation 16, through the window 7 in the thermostatically controlled chamber 1. Sources of UV radiation, like UV-spectrum LEDs, are used as the means of illumination 12. The excitation filter provides detaching of the mark fluorescence spectrum from the spectrum of the means of illumination 12.

The device operates as follows. The temperature in the thermostatically controlled chamber 1 is set and maintained at a fixed level, and the cuvette 2 placed inside of it is uniformly warmed up. Before the test, a sample, for example plasma, is placed into the cuvette 2. When the same temperature has settled within the whole volume of the sample, and the convective streams in it have stopped, the insert 4 is placed inside the cuvette so as to bring the thrombogenic agent applied on the end of the said insert 4 into contact with the sample and to initiate the studied coagulation process.

The thermostatically controlled chamber 1 is closed with the means of pressurization 6, and excess pressure in the chamber is created using the means 5 of pressure regulation. During the study, the light trap 11 provides efficient absorption of the radiation passing behind the cuvette 2 plane due to geometry and surface behavior thereof providing repeated re-reflection and absorption of the background radiation so that the reflected radiation does not get back into the registration area of the cuvette 2 and into the entrance aperture of the lens 10. Images of the clot growing inside the cuvette 2 are delivered through the transparent window 7 and the lens 10 to the means of registration 9. After that, digitized images are delivered into the memory of the means 13 for further digital processing of results.

If, for example, fluorogenic substrates are added into the test sample, the latter is illuminated at determined moments by the means of illumination 12 to excite fluorescence of the mark, and spatial distribution of fluorescence of the mark in the sample is registered by the means of registration 9. Specially developed software allows the unit of control of the means of illumination and registration to turn on the means of illumination 8 and/or 12 for only a short time when the recording is performed. Such operating regime of the means of illumination reduces the effect of photo-discoloration of the substrate mark. Simultaneously with illumination of the substrate mark, the test medium sample is illuminated by the means of illumination 8 to register optical parameters of the test sample selected from the group consisting of: spatial distribution of light scattering, spatial distribution of light transmission within the sample, or a combination thereof. Thereby, spatial distribution of blood coagulation parameters, in particular, spatial distribution of fibrin, is registered. It is to be noted that the illumination wavelength is selected in accordance with the excitation spectrum of the mark in case if the fluorescence is studied, or in accordance with the spectrum of light scattering and sensitivity of the means of registration in case if the light scattering is registered.

Thus, the claimed device allows more accurate and detailed study of all stages of the coagulation process in time and space, increasing the accuracy and the reliability of clinical assessments of the test samples under normal and different pathological conditions.

The invention claimed is:

1. A device for monitoring of spatial coagulation of blood and its components comprising:
   a thermostatically controlled chamber filled with a transparent substance suitable for temperature regulation, wherein the thermostatically controlled chamber is pressure sealed,
   a cuvette filled with a sample of a test medium, wherein the cuvette is placed in the thermostatically controlled chamber,
   at least two means of illumination having different radiation wavelengths, wherein at least two means of illumination comprises the first means of illumination illuminating the sample of the test medium to induce light scattering from the sample, and the second means of illumination illuminating the sample of the test medium with the excitation radiation to excite fluorescence in the sample,
   a means of recording, wherein the means of recording and the at least two means of illumination are placed together in front of the cuvette on one side of the thermostatically controlled chamber, and
   a means of pressure regulation connected to the thermostatically controlled chamber and to the cuvette,
   wherein the thermostatically controlled chamber includes a light trap, wherein the light trap is formed by the geometry and light absorbing properties of the inner surfaces of the thermostatically controlled chamber, and provides repeated re-reflection and absorption of the radiation passing behind a cuvette plane, and
   the light trap is placed on the side opposite to the means of recording and the at least two means of illumination behind the cuvette, and the means of pressure regulation are configured for maintaining excess pressure in the thermostatically controlled chamber and in the cuvette to exclude the formation of gas bubbles during heating of the sample of the test medium.

2. The device according to claim 1 further comprising optical elements, which direct, focus and provide spectral correction of the illumination.

3. The device according to claim 1 further comprising a control unit for synchronizing performance of the at least two means of illumination, a means of recording and a means of pressure regulation.

4. The device according to claim 1 further connected to a means of processing the test results.

5. The device according to claim 1, wherein the pressure is in a range from 0.2 to 0.5 atm.

6. The device according to claim 1, wherein the substance suitable for temperature regulation is selected from the group consisting of: fluid, air, or gel.

7. The device according to claim 6, wherein the fluid is water.

8. The device according to claim 1, wherein the one side of the thermostatically controlled chamber in front of the cuvette includes a transparent window through which the at least two means of illumination illuminate the sample.

* * * * *